United States Patent
Nebosis et al.

(10) Patent No.: US 10,912,533 B2
(45) Date of Patent: Feb. 9, 2021

(54) HIGH-SPEED MAGNETIC SYNCHRONIZATION OF WIRELESS DETECTOR

(71) Applicant: AGFA NV, Mortsel (BE)

(72) Inventors: Rainer Nebosis, Mortsel (BE); Dirk Vandenbroucke, Mortsel (BE)

(73) Assignee: AGFA NV, Mortsel (BE)

( * ) Notice: Subject to any disclaimer, the term of this patent is extended or adjusted under 35 U.S.C. 154(b) by 0 days.

(21) Appl. No.: 16/634,617

(22) PCT Filed: Jul. 31, 2018

(86) PCT No.: PCT/EP2018/070787
§ 371 (c)(1),
(2) Date: Jan. 28, 2020

(87) PCT Pub. No.: WO2019/025463
PCT Pub. Date: Feb. 7, 2019

(65) Prior Publication Data
US 2020/0268340 A1    Aug. 27, 2020

(30) Foreign Application Priority Data
Aug. 2, 2017    (EP) .................................... 17184478

(51) Int. Cl.
*A61B 6/00*    (2006.01)

(52) U.S. Cl.
CPC .................. *A61B 6/56* (2013.01); *A61B 6/40* (2013.01); *A61B 6/542* (2013.01)

(58) Field of Classification Search
CPC .............. A61B 6/56; A61B 6/40; A61B 6/542
See application file for complete search history.

(56) References Cited

U.S. PATENT DOCUMENTS

| | | | | |
|---|---|---|---|---|
| 4,768,215 A | * | 8/1988 | Kiwaki | H01J 35/165 174/85 |
| 7,436,444 B2 | | 10/2008 | Endo | |
| 2012/0128127 A1 | * | 5/2012 | Chicchetti | A61B 6/4405 378/62 |
| 2013/0301801 A1 | * | 11/2013 | Liu | H05G 1/08 378/91 |
| 2013/0301803 A1 | | 11/2013 | Liu et al. | |
| 2015/0164459 A1 | | 6/2015 | Ito | |
| 2020/0046310 A1 | * | 2/2020 | Richard | A61B 6/4208 |

OTHER PUBLICATIONS

Official Communication issued in International Patent Application No. PCT/EP2018/070787, dated Dec. 7, 2018.

* cited by examiner

*Primary Examiner* — Edwin C Gunberg
(74) *Attorney, Agent, or Firm* — Stinson LLP (57) ABSTRACT

Mechanisms for synchronizing the read-out sequence of non-tethered digital X-ray detectors in a radiography system with an X-ray generator or an X-ray source for use in digital wireless detectors where a synchronization of the digital wireless detector circuitry with the start of the actual exposure is required. The mechanisms can be applied in X-ray devices that are based on digital flat panel detectors, and wherein the digital detectors do not have a tethered connection with the modality for receiving the activation signal.

14 Claims, 2 Drawing Sheets

HIGH-SPEED MAGNETIC SYNCHRONIZATION OF WIRELESS DETECTOR

CROSS REFERENCE TO RELATED APPLICATIONS

This application is a 371 National Stage Application of PCT/EP2018/070787, filed Jul. 31, 2018. This application claims the benefit of European Application No. 17184478.0, filed Aug. 2, 2017, which is incorporated by reference herein in its entirety.

BACKGROUND OF THE INVENTION

1. Field of the Invention

This invention is related to digital radiography acquisition systems used for medical and non-medical uses. Reference is made in the embodiments to particular examples in medical imaging.

2. Description of the Related Art

General radiology has widely embraced wireless digital detector technology over the past years, allowing it to penetrate in many segments of the radiography systems market. The integration of microelectronics circuitry, new battery technology and technologically matured direct radiography detectors in an appealing packaging allowed the development of less costly and reliable digital and wireless radiography detectors, which offer the advantage of portability and superior image quality for many applications.

Digital radiography (DR) is a form of X-ray imaging, where digital X-ray sensors are used instead of traditional photographic film or cassette based CR systems. Advantages include time efficiency through bypassing chemical processing (compared to traditional film based systems) and through immediate read-out of the image data from the sensor (compared to cassette based CR systems where the read-out of the detector is done by means of a dedicated digitizer system). Fast readouts of the detector also allows the acquisition of fast sequences of images, which allows application such as dynamic imaging and for instance tomosynthesis.

The advantages of the DR design include compact size and immediate access to digital images. Also the X-ray conversion efficiency of DR systems greatly exceeds the performance of CR systems, which have conversion efficiencies of 20-35%, and of screen-film systems for chest radiography, which have nominal conversion efficiencies of 25%. Also the ability to digitally enhance images are important advantages of digital systems. DR sensors (direct radiography sensors) or flat panel sensors exist in 2 different categories; indirect and direct flat panel sensors. 3.

Direct flat panel sensors convert X-ray photons directly into an electric charge. The outer layer of this type of sensor in this design is typically a high-voltage bias electrode. X-ray photons create electron-hole pairs in a-Se (amorphous Selenium), and the transit of these electrons and holes depends on the potential of the bias voltage charge. As the holes are replaced with electrons, the resultant charge pattern in the selenium layer is read out by a TFT array, active matrix array, electrometer probes or microplasma line addressing.

Indirect flat panel sensors combine an a-Si (amorphous Silicon) sensor with a scintillator in the sensors outer layer. The scintillator typically consists of caesium iodide (CsI) or gadolinium oxysulfide ($Gd_2O_2S$) which transforms the incident X-rays into visible light. This visible light is channeled through the a-Si layer which converts it to a digital output signal by means of a TFT (thin film transistor) array.

A particular technical characteristic of any DR sensor is that (as opposed to a CR sensor or conventional screen film techniques) an active signal needs to be sent to the DR sensor (called "trigger") to signal it that the exposure will start. The trigger signal puts the DR sensor in a state that it starts accumulating charges generated by the irradiation source, to build up the radiographic image. Also, the duration information of the exposure is sent to the DR sensor to allow it to stop the image acquisition cycle after a predetermined period of time. The reason why it is necessary to make sure that the acquisition time is limited to the exposure time only, is that in a DR sensor, even in a state when it is not subjected to X-rays, charges are accumulated unwillingly which will contribute to the image read out at the end of the cycle. It is clear that these unwanted charges will contribute to the noise in the image. The source of these unwanted charges are dark currents and alike, these charges are accumulated in DR sensor portions that detect the X-rays. Therefore, it is important to limit the acquisition time to the duration of the exposure only. In most DR sensors, this acquisition state is preceded by a phase during which the unwanted accumulated charges causing background noise in the image are erased from the sensor, before it can be put in the acquisition phase. A second aspect to be considered is the read-out period of the panel. During the read-out phase the detector is still accumulating charges if exposed. But a small portion of the detector is insensitive as it is reading the charges. This small region is moving over the complete detector area. In case a series of images is recorded and the detector is exposed to X-ray radiation during the read-out phase the image assignment is wrong.

Consequently, it is important that the DR sensor is switched to it's acquisition state as soon as the irradiation starts, but not before and that exposure is switched off during read-out phase if required. The acquisition state should be switched to read-out state when irradiation ends. In case the DR sensor would be switched on too late, only a fraction of the irradiated dose would contribute to the radiographic image leading to a suboptimal image quality of the acquired image (or even worse, the acquisition would not detect any irradiation, and no image would be generated). In case the radiation would be switched off too late a part of the collected charges would be assigned to the next image in a sequence or a part of the collected charge would not be used for the image information for recording of a single image.

The potentially detrimental effect of the above mentioned timing issues become even more important in applications where a fast sequence of accurately timed exposures are to be captured by the X-ray detector 'in sync' with a sequence of X-ray pulses generated by the X-ray generator. Deviations in timing between the actually intended trigger moment and the received trigger by an X-ray detector panel is called 'jitter'. The origin of the jitter can be found in the sum of the latencies of the different components in the signal transmitting chain.

In a typical fixed (non-mobile) DR system and in its simplest implementation, the DR sensor is triggered by means of an electrical signal running over a tethered (or wired) connection from the X-ray generator to the DR sensor. The electrical signal is sustained during the full duration of the X-ray exposure, which implies that the DR detector is also able to detect when the exposure cycle ends (namely when the electrical signal is broken off). The advantage of this tethered trigger connection is that it is very reliable, very simple in its implementation and that it does almost not suffer from any latency effects.

Wireless digital X-ray sensors are DR sensors assemblies which can operate without being physically connected by a wire to a workstation. It is noted here that the term "DR sensor" refers only to the bare detection device, whereas the "digital X-ray sensor" refers to a complete assembly comprising a "DR sensor" as its main component. The type of DR sensor assemblies referred to above are typically not integrated into the bucky of a positioning device or a table, and offer their advantage in that they can be handled in a similar way as CR detectors, at least from a usability point-of-view. Wireless digital X-ray sensors have become commercially available since 2009. With wireless digital X-ray sensors, it is mandatory to use some sort of digital communication technique between the wireless digital X-ray sensor and the workstation console in order to transmit the data regarding the exposure time (which is required for the configuration of the panel), to give a number of timing trigger signals (e.g. to initiate the preparation cycle, and to trigger the start of the acquisition), and eventually to read out the acquired image data. Examples of such digital communication techniques are Wi-Fi or Bluetooth, which allow bi-directional transmission of data. The wireless DR sensor assembly includes a built-in battery to supply power to the detector and controller electronics. The battery allows the sensor's necessary autonomy to obtain several radiographs and to transfer the obtained radiographs to the acquisition workstation for further viewing. This way each performed radiograph is transferred at almost real time from the wireless DR sensor to the workstation.

A known problem with wireless digital X-ray sensors is that it is difficult to implement a suitable trigger mechanism to accurately transfer the start signal of the actual X-ray exposure initiated by the X-ray generator to the digital X-ray sensor, and to avoid latency problems. As explained above, an accurate synchronisation of the acquisition cycle of the DR sensor and the X-ray exposure period is essential to optimally utilize the emitted X-ray radiation for the purpose of the intended image acquisition. This means that any (risk of) latency effect in the transmission of the trigger signal between the X-ray generator and the DR sensor side should be avoided. This requirement makes the above mentioned generic digital communication techniques unsuitable to serve as technique to transmit the trigger signal; both said communication techniques are known to suffer from latency problems especially in congested wireless network environments. Typical latency of Bluetooth communications is 200 ms, whereas latency of Wi-Fi is 150 ms, but these values are known to vary depending on the saturation of the radio transmission band (contention) and poor channel conditions. Since the typical exposure time for a chest, abdomen and spine acquisition are respectively 0.1, 0.15 and 0.2 seconds, it is clear that the latencies for Wi-Fi and Bluetooth are unsuitable for the intended purpose. To take the example of Wi-Fi, the communication is based on the WLAN protocol (IEEE802.11) which inherently operates asynchronously and independently between devices. In order to improve the latency for Wi-Fi, it would be required to implement an additional synchronization mechanism. (Recently, a solution based on Wi-Fi has been proposed by Texas Instruments known as WL8 (in their software release R8.6) which accomplishes a time accuracy of less than 20 µs. This solution is however not commercially available today in DR detector products.)

Because of the above mentioned latency and jitter problems, different approaches to circumvent the latency problems in known wireless communication techniques have been developed and are being reported on in the literature. In wireless digital X-ray sensors, the trigger mechanism to start the acquisition may for instance be generated within the wireless digital X-ray sensor itself. This technique relies on a very fast early detection of incoming X-ray radiation by the DR detector, whereby no separate and parallel signal is required to signal the start of the exposure. The actual X-ray exposure thus triggers the wireless DR sensor as soon as possible to start the acquisition state of the wireless DR sensor. The many implementations described in the art mostly rely on mechanisms whereby a radiosensitive element in the wireless DR sensor assembly detects incoming radiation, and will self-trigger the imaging sensor upon exceeding a measured radiation threshold value. U.S. Pat. Nos. 7,436,444 and 5,887,049 describe an implementation of such a self-triggering mechanism of a wireless DR sensor whereby a dedicated radiosensitive element measures the incident exposure irradiation and will cause a driving circuit to generate the trigger as soon as a measure dose threshold value is exceeded.

US2014/0086391 describes a similar implementation of a self-trigger mechanism for a single wireless DR sensor, but in this case multiple areas of the detector area of the DR sensor are used to detect the incident irradiation. Different areas of the DR sensor are used in order to have the area where the irradiation threshold is exceeded first trigger the entire sensor to start the image acquisition. This method allows for a higher probability to detect the start of the X-ray irradiation as soon as possible, and thus to self-trigger the wireless DR sensor in time.

U.S. Pat. No. 6,972,411 describes another implementation of a self-trigger mechanism for a single detector in an intraoral application whereby the trigger signal is taken from a measurement of the total amount of current drawn from the entire detector. The entire area of the DR sensor is used to monitor the start of the X-ray exposure.

While the abovementioned self-triggering techniques ensure a reliable triggering of the DR sensor, a part of the X-ray signal is by definition sacrificed for the trigger signal, the part being ultimately discarded for contributing to the image acquisition itself. In case of recording a sequence the self-triggering additionally heats up the detector (the detector is always keep in a "ready mode" which is power consuming). Heating the detector is reducing image quality and in case of a sequence leads to a decreasing image quality from start to end of the sequence.

US2015/164459 A1 describes an automatic exposure control circuit, wherein a sync communication interface based on radio waves is disclosed to establish communication signals with the AEC.

US2013/301803 describes an X-ray system in which an inductive system provides contactless power transmission to a digital portable X-ray detector. The inductive system is foreseen with circuitry to limit electromagnetic interference in the detector, which may cause artefacts in the generated image. In this disclosure, data may be transmitted by means of capacitive transmission avoiding the need for wired contacts. Such capacitive transmission operates only at very close distances between sender and receiver.

SUMMARY OF THE INVENTION

The present invention provides a system for transmitting a trigger signal from an X-ray generator to a wireless digital X-ray sensor to initiate the capturing of a digital image sequence, as set out below.

In the context of this invention, a trigger signal from an X-ray generator has to be understood as the electrical or other type of signal, such as an audible, optical, magnetic signal, which is produced by the X-ray generator of an X-ray system to indicate that it will actually start to provide a high voltage current to the X-ray tube for the exposure. The generator of an X-ray system is the electrical high voltage component that controls the powering of an X-ray tube. The X-ray generator can only be activated when all safety and other technical conditions are fulfilled to drive the X-ray tube with a very high electrical current load so for it to produce X-rays. The generator typically is activated by a manual switch operated by the radiographer, and has 2 contact modes, the first being activated upon slightly pressing the button and activating the so-called "prep-mode" of the generator, and the second being activated at full suppression of the button and activating the actual exposure. It is this second contact mode that is considered the actual signal for the X-ray generator to release the electrical current.

On condition that the generator successfully passed all internal conditions and is about to actually start the exposure, the above mentioned trigger signal from the X-ray generator is given to the wireless digital X-ray sensor to indicate that the actual exposure starts (and that the digital X-ray sensor has to start integrating the captured photons). The "prep-mode" signal issued by the radiographer allows the X-ray generator electronics to prepare the exposure by a.o. charging some of its electrical components, and to start checking readiness and security features of the generator. The "prep-mode" brings the generator in a state that allows it to immediately deliver the burst of electrical current when triggered by the second contact mode of the operator switch.

A magnetic coil for generating a magnetic field has to be understood as a typically coiled or solenoid conducting wire that is characterised by its number of windings and thickness of the wire. It is known that when such a magnetic coil is driven with an electric direct current a magnetic field is generated that is sustained for as long as the direct current is maintained. An alternating magnetic field can be induced when applying an alternating current to the coil. A similar type, but not necessarily the exact same type, of magnetic coil is used for detecting the magnetic field at the receiver component side. The invention is not limited to the use of "classical'" coils. Dependent on the working frequency adapted geometries can be used which might significantly differ from solenoids.

The inverse phenomenon—called "magnetic induction"—is also known in that when a magnetic field is applied to a magnetic coil, an electric current is generated in the coil for as long as a there is a change of the applied magnetic field. The change in magnetic field will result in a temporary current pulse that can be measured and used as a transmitted signal or trigger. When an alternating magnetic field is applied on such a coil or solenoid, the pulses of measurable current generated in the coil will occur at the same frequency of the alternating inducing current of the sender coil. Again the invention is not limited to the use of "classical'" coils consisting of a solenoid conducting wire. Dependent on the working frequency, adapted geometries can be used which might significantly differ from solenoids. For simplicity in the following, the generator and receiver assemblies are called coils or solenoids.

Such a magnetic coil generates a magnetic field when the coil is energized by means of applying an electric current on opposite ends of its windings. The strength of the magnetic field $\vec{H}$ depends on the strength of the current applied, the dimensions of the coil and the number of windings.

Such an electric current is applied by a device or component that generates the desired current and voltage, called the magnetic coil driver. This magnetic coil driver is a piece of electronic circuitry that produces the desired output current when activated. The magnetic coil driver referred to in the sender component has to be understood as an electronic device or component that is configured to generate an electrical current in the magnetic coil of the sender component. The electrical current shall be controlled by a microcontroller (see further).

The microcontroller [210] or [310] referred to in this disclosure is a small computer that may reside on a single integrated circuit or may be embodied as separate components, and comprises one or more CPUs (processor cores) along with memory, a digital clock and programmable input/output peripherals. Program memory in the form of Ferroelectric RAM, NOR flash or OTP ROM is also often included on chip, as well as a small amount of RAM. The digital clock [212] and [312] may be an integral part of the microcontroller, or be embodied as a separate device or component digitally connected to the microcontroller. Moreover the microcontroller may comprise a bi-directional wireless data communication means (Wi-Fi, Bluetooth or other) [211] or [311] to communicate with the receiver. The microcontroller may also comprise or connect to an analog or digital trigger module [213] or [313] which respectively generates [401] or receives [101] a trigger-output toward the X-ray sensor [400] or respectively from the X-ray generator [100].

The wireless digital X-ray sensor [400] referred to in this application has to be understood as a fully integrated and independently operational wireless, battery powered digital X-ray sensor assembly. The term wireless digital X-ray sensor has to be thus understood as a full assembly comprising more than only the bare X-ray detector panel itself; the wireless digital X-ray sensor has to be understood as the X-ray detector panel complemented with a.o. a controller having wireless communication means (Wi-Fi, Bluetooth or other) for operating the different components and processing the raw image data, a memory for storing temporarily the acquired images, a battery for operating the device, a casing or packaging keeping all components together, and others. It can be envisaged that certain components of the digital X-ray sensor may be shared with the receiver component [300] to perform some of its functions. As such, it may be envisaged that the microcontroller, clock, memory, wireless data communication means or other parts would be fully integrated or shared between the digital X-ray sensor functions and the trigger receiver component. The same counts for the sender component [200] which in its turn may share components with the X-ray generator or X-ray console [100] in which it may be fully integrated.

The electrical signal converter referred to in the receiver component has to be understood as an electronic device or component that is configured to amplify the magnetically induced current in the magnetic coil of the receiver component, followed by quantization of the measured amplitude of the amplified signal. This quantization is typically performed by a so-called A/D-converter (analogue-digital converter) which is known in the art, and transforms the analogue measured amplitude value (a real number value) into a discrete value. The same A/D-converter also performs the sampling process that happens at a certain frequency (the sampling frequency), and results in a digital discrete-time signal, referred to in this application as the continuous digital signal stream. Moreover, and as stated above, the receiver circuit may comprise an analogue or digital trigger module [313] which generates a trigger-output toward the digital X-ray sensor, a digital communication path (Wi-Fi, Bluetooth or other) [311] to communicate with the generator, and/or a digital clock [312].

Further advantages and embodiments of the present invention will become apparent from the following description and drawings.

BRIEF DESCRIPTION OF THE DRAWINGS

At the other end of imaging chain of the X-ray system resides the X-ray detector, which is in our embodiment of the invention a wireless digital X-ray sensor [400]. The wireless digital X-ray sensor [400] is shown comprising an integrated and miniaturized version of the receiver component [300], and is shown as a small grey compartment in the wireless digital sensor [400]. The trigger signal that is propagated by the invention to activate the digital X-ray sensor is shown as an arrow [401], and is generated within the receiver component [300] by the analog or digital trigger component [313].

It has to be understood that the wireless digital sensor [400] comprising the receiver component [300] is physically separated from the X-ray systems generator or console [100] that comprises in its own turn the sender component [200]. There is thus no physical or tethered connection between the two parts of the system.

The sender component [200] is drawn showing its different components: the sender microcontroller [210], the magnetic coil driver [220] and the magnetic coil [230], generating a magnetic field $\vec{H}$ [600]. The sender microcontroller [210] is shown comprising a digital clock [212], a digital or analog trigger module [213], and optionally comprising a wireless communications module [211].

The receiver component [300] comprises the following components: a magnetic coil [330] outputting a measurable electric current [331], an electrical signal converter [320] comprising an electric current amplifier and an A/D-convertor (indicated by the universally used symbols of said components) outputting the continuous digital signal stream [321], and receiver microcontroller [310] configured to receive said continuous digital signal stream from the electrical signal converter [320], and configured to trigger said wireless digital X-ray sensor [400] to which it is connected (or in which it is integrated). The receiver microcontroller [310] is shown comprising a digital clock [312], a digital or analog trigger module [313], and optionally comprising a wireless communications module [311].

In this embodiment, as can be seen in the drawing, there are three different magnetic coils [230] present that are moreover orthogonally oriented with respect to each other. A similar set of three orthogonally oriented magnetic coils [330] are also present in the receiver component.

DETAILED DESCRIPTION OF THE PREFERRED EMBODIMENTS

The purpose of the invention herein disclosed is the reliable and accurate synchronization of the start of an exposure that is produced by an X-ray generator with the start of the acquisition cycle of the same exposure by a wireless digital X-ray sensor. A trigger signal [101] given at the X-ray generator or console by a user marks the actual starting point in time to start an X-ray exposure, next to which this exposure is also characterized by a certain duration. Two different approaches or "trigger methods" may be chosen to ensure an accurate synchronisation of the start of the exposure by the X-ray modality and the start of the acquisition cycle of the wireless digital X-ray sensor.

In a first trigger method, which we will call "direct synchronization", the trigger signal [101] initiates the actual exposure in the X-ray generator, while at the exact same moment and with the lowest possible latency the same trigger [101] is propagated by the magnetic field $\vec{H}$ [600] to the digital X-ray sensor [401]. The trigger signal thus simultaneously activates the exposure and the acquisition cycle of the digital X-ray sensor. The mechanism to wirelessly propagate this trigger signal to the digital X-ray sensor is discussed in more detail below.

In a second trigger method, which we will "indirect synchronization", the trigger pulse propagated by the magnetic field $\vec{H}$ [600] may be used to synchronize the clocks of a generator and a receiver component [212] and [312], after which a timing (or sequence of timings) for future synchronized events is communicated to the respective X-ray generating and X-ray sensor components via a (less time-accurate) bi-directional wireless data communication means (such as Wi-Fi, Bluetooth, and alike). In this mechanism, the accurate synchronization mechanism is used only to accurately synchronize the clocks, and not to trigger the actual events.

The duration and/or start of the exposure (or exposure time) is known upfront and chosen by the operator of the system. This exposure time and other exposure parameters are programmed in the X-ray system console prior to giving the exposure command. The X-ray generation components (X-ray generator and X-ray tube) are designed such that there is a very low latency between the moment that the trigger switch is activated (by closing an electrical contact) and that X-ray radiation is produced by the tube. This is crucial, as the operator requires the accurate control over the moment of exposure in case of direct synchronization. In case of indirect synchronization via the clocks of the generator and receiver this crucial control is guaranteed by transferring the absolute time-stamps of exposure prior to the start of the sequence. As long as the generator and receiver clocks are synchronized this enables an undelayed operation.

Another important feature of the X-ray generator is that it can very accurately sustain the produced high voltage current fed into the X-ray tube for a very accurately timed duration. Also here, accuracy is very important in order to accurately control the delivered dosage to the patient during his exposure. In fact, the beam forming components are designed with low trigger latency and timing accuracy in mind.

In order to optimize the digital image capture by the digital X-ray sensor, it should be ensured that the acquisition period (or dose integration period) of the DR sensor is synchronized with the actual exposure period of the X-ray source. This means that both the start and the duration of the acquisition (integration) time of the DR sensor and the exposure time of the X-ray generator should be ideally identical. This also ensures that no X-ray emission is present during read-out of the DR sensor in the digital X-ray sensor.

In fixed, tethered DR-based X-ray systems, this can easily be achieved by transmitting the trigger signal over a wired connection to activate the digital X-ray sensor, as for such a wired connection there is close to no latency in the transmitted signal. Our invention however allows for transmitting a comparable low latency trigger signal in a wireless setup.

In a first embodiment, the transmission of a single trigger signal is performed by the transmission of a single magnetic pulse between a sending and receiving part of the invention. The advantage of using a magnetic pulse to carry the signal is that there is close to no latency between the generation of the magnetic pulse, signal or sequence of signals and the reception of such a signal by a magnetic coil in the receiver component.

The operating principle of the invention comes from the surprising effect that the latency of a transmitted trigger signal based on magnetic principles is very low, and thus can fulfil the application requirements of traditional (still) X-ray acquisitions or dynamic imaging. For dynamic images, the requirements towards low latency and consequently low jitter are even more stringent, so that the advantages of applying the invention are even more pronounced.

Nevertheless, in order to ensure reliable operation of such a magnetic pulse based transmission system, certain measures have to be taken to ensure that the magnetic trigger signal is sufficiently strong and detectable by the receiver electronics.

Figure 1:
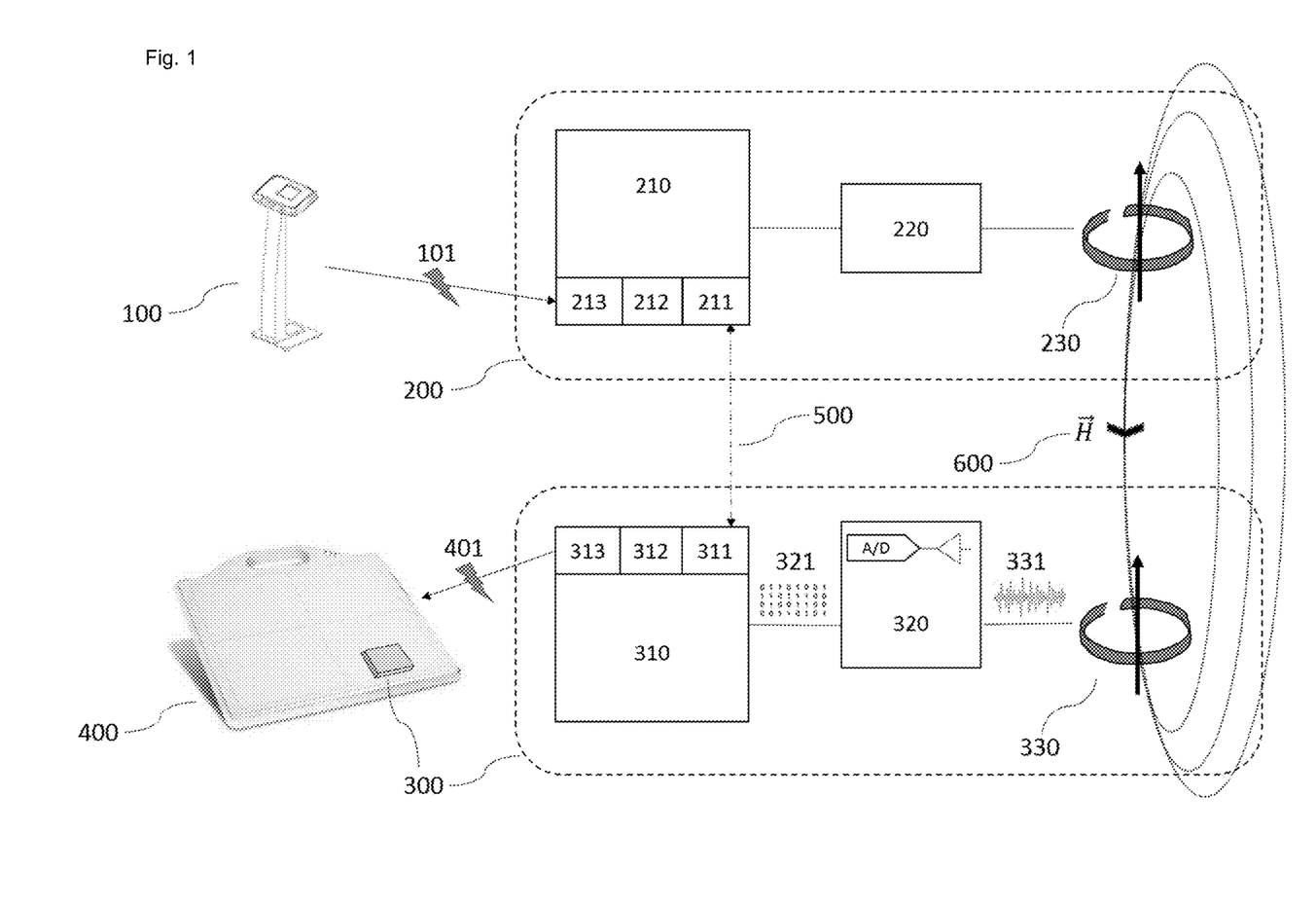
FIG. 1 gives a schematic overview of a first embodiment of the invention using only 1 magnetic coil [230] in the sender component [200] and 1 magnetic coil [330] in the receiver component [300], and showing the sender component [200] and the receiver component [300] in the context of their usage within a X-ray system. The X-ray systems generator that is responsible for giving the trigger signal [101] to the detector is here represented by the console [100] component of a typical X-ray system. The console is connected to the X-ray generator (not shown) and serves as the user as an interface through which the actual trigger command is given by the radiographer.
Figure 2:
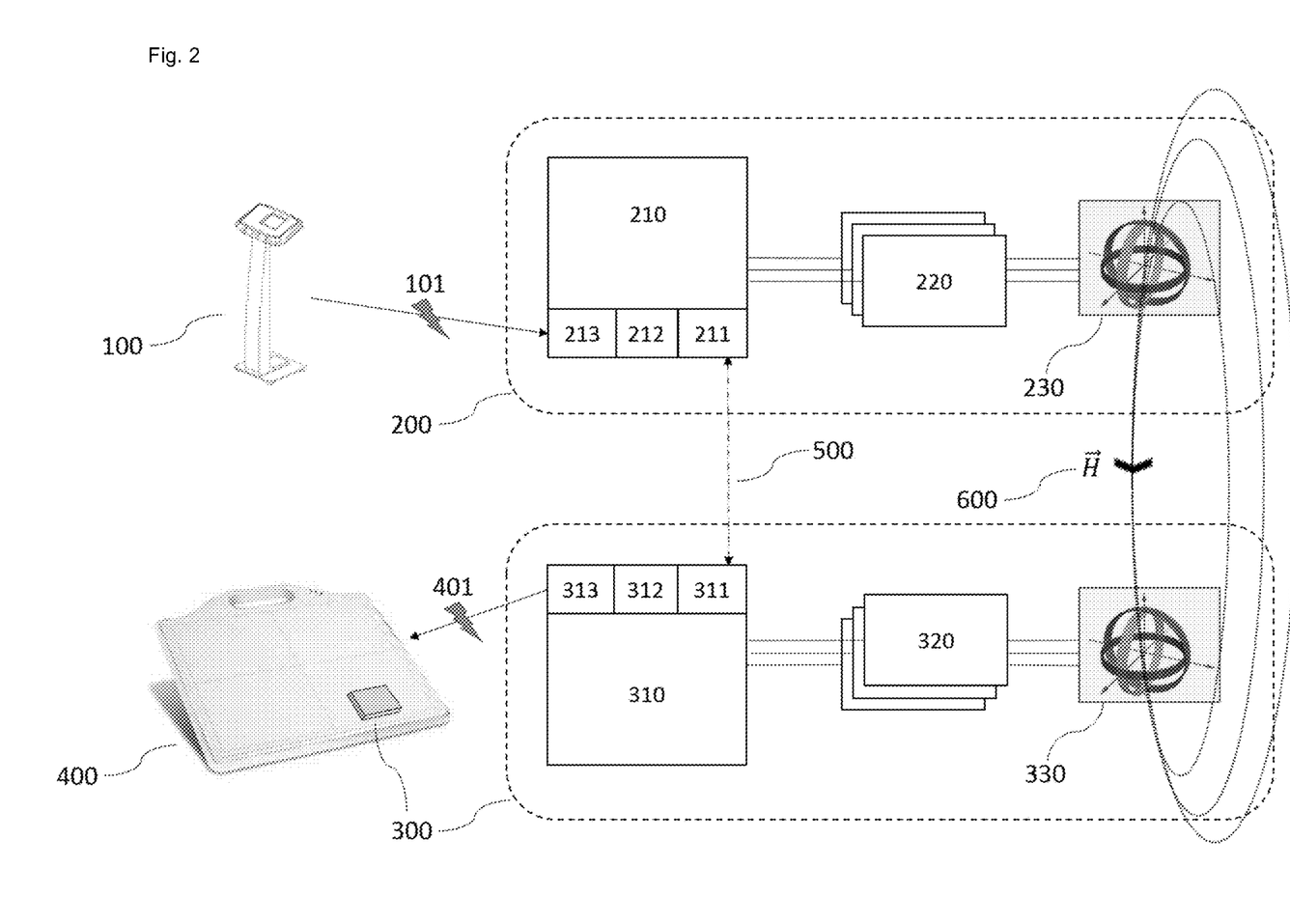
FIG. 2 gives an equivalent overview of a second embodiment of the invention, wherein multiple magnetic coils [230] are integrated in the sender component [200] and are each driven by an individual magnetic coil driver [220]. Similarly, the receiver component [300] comprises multiple magnetic coils [330] picking up individual measurable electric currents [331] by the multiple electrical signal converters [320] for each magnetic coil, and that are subsequently digitized into a continuous digital signal stream [321] or set of digital signal streams [321] for each magnetic coil. The continuous digital signal stream [321] is monitored and analysed by the microcontroller [310] that comprises an optional wireless communication module [311].

In this first embodiment of the invention, a single magnetic coil [230] produces a single magnetic field [600] of which the direction is oriented in the direction of the axis of the coil. As soon as the magnetic field is generated by energizing the magnetic coil by an electric current, the magnetic field raises and has a particular strength and orientation (mathematically represented as the magnetic field vector $\vec{H}$). The detection of the magnetic field by a magnetic field detector [330] is direction dependent, and depends on the coupling efficiency between the 2 magnetic coils. In certain positions and under certain orientations a magnetic detector may measure an optimal signal (with maximal signal amplitude) as the consequence of an optimal coupling between the two magnetic coils [230] and [330]. The coupling efficiency of two magnetic coils depends on their mutual orientation and relative distance. So there are relative orientations between a generator magnetic coil and a receiver magnetic coil which result in very small signals even when they are close to each other. So, our first embodiment of the invention (when using a set of single coils) can only work reliably on condition that the relative positions and orientations of the sender and receiver coils can be controlled. Therefore, this first embodiment should be used preferably for application in an "indirect synchronization" trigger method, wherein the digital X-ray sensor would be temporarily brought into a known position relative to the sender component during the synchronizing process of the clocks of the sender and receiver components. This known "synchronization position" is specifically chosen to ensure an optimal magnetic coupling between sender and receiver coils.

This can be practically achieved by making sure that the magnetically coupling coils are brought physically close together and in the right orientation when bringing the modality in its parking position. A parking position of a modality is an inoperative or rest position, and is the physical configuration in which a mobile X-ray modality can be brought by flexing the tube arm in a specific position in order to make the system more compact for more easy transportation, to avoid collisions and to provide more stability when moving the system around. Such a parking position brings the collimator head in a particular and predefined position close to which a storage location can be foreseen to carry and store the digital X-ray sensor. The magnetic coils of the sender component would in this configuration typically be integrated in (or close to) the collimator head, while the magnetic coils of the receiver component are integrated into the digital X-ray sensor. The orientation of the coils can then be chosen such that the optimal magnetic coupling is achieved.

Another problem relating to the measurement of magnetic field strengths is the influence by external magnetic disturbances, such as the presence of metallic objects in the vicinity of the sensor coil. Such disturbances have not so much an impact on the amplitude component of the magnetic field vector, but rather on the direction of the magnetic field vector. This means that such disturbances nevertheless can have a significant impact on the measured amplitude by the sensor coil in a certain position. This is another reason why relying on the amplitude measurement of a single magnetic sensor alone is not sufficient to reliably transmit a trigger signal, unless such disturbances are being actively avoided by preventing their occurrences such as for instance when using a known calibration position of the digital X-ray sensor as explained above.

External magnetic disturbances could occur due to a positioning of the magnetic sensor coil near electric transformers or other electronic equipment, or even due to the presence of the static magnetic fields, such as the earth's magnetic field. Also, metallic objects in the vicinity of the magnetic coil of the receiver component may cause undesired magnetic disturbances, or shield off the intended magnetic field trigger pulse.

In a second embodiment, the problem of magnetic disturbances is resolved by means of using alternating magnetic fields for propagating the trigger signal, rather than a single static magnetic field. The reason for using alternating magnetic fields as opposed to static magnetic fields is that this approach compensates for the presence of any static magnetic field, such as the earth's magnetic field in case that the amplitude of the received signal is taken as the parameter for distance measurement. Also when choosing the appropriate frequency of the alternating magnetic signal, the effect of disturbances by alternating magnetic fields can be suppressed. The appropriate frequency should be chosen such that it stays away from potentially interfering alternating magnetic fields, such as the frequency at which electrical appliances such as transformers operate (50-60 Hz). The frequency should preferably be higher then 1 kHz (as the lower boundary), and should also not exceed 30 MHz, the point after which water and human tissue starts to absorb energy Within this very wide frequency band, radio frequencies should be avoided for obvious reasons.

For the application of this improvement, it is contemplated to use resonant magnetic signal generator- and sensor-pairs to optimize the magnetic signal transfer for triggering. In a preferred embodiment, the signal generator is a coil through which an alternating electric current is sent by a magnetic coil driver. The alternating electric current induces an alternating magnetic field of the same frequency that can be detected at a distance from the magnetic coil of the sender component. A similar or smaller coil is used as the signal sensor of the receiver component and picks up the alternating magnetic field passing though it; inversely the alternating magnetic field induces an alternating current in the sensor coil that can be picked up and measured. The detector coil may be smaller in size and have a different winding number in comparison with the generator coil. The circuit that reads out the alternating electric current in the sensor coil is "tuned" to the frequency of the generator (hence the name "resonant") by means of the selection of the correct capacitor and resistor network, in order to optimize the sensitivity to the generator signal frequency.

While in the above preferred embodiment, the magnetic generator and resonant magnetic sensors are coils, different types of magnetic sensors may be used as alternatives, such as MEMS, Hall effect based sensors, magneto-resistive sensors, or alike . . . .

The amplitude of the measured alternating current in the resonant magnetic sensor has a relation with the distance between the signal generator and signal sensor. The amplitude is approximately inversely proportional to the cubic distance from the signal generated, when measured in radial direction from the generator. When the sensor coil is kept at the same distance to the generator but its orientation and/or the relative orientation is changed the received signal ranges from 100% to 0%.

In a third and preferred embodiment, instead of one single magnetic coil to generate the magnetic field, a set of differently oriented magnetic coils is used to overcome the earlier described problem of the direction sensitivity of the signal amplitude. Where it was described above that the successful detection of a magnetic trigger signal using a single magnetic coil is strongly dependent on the respective orientation of the magnetic coil in the sender component relative to the orientation of the magnetic coil in the receiver component, the following embodiment tries to overcome this problem, by proposing a solution wherein the trigger signal is no longer direction dependent.

In this embodiment, a combination of differently oriented magnetic coils is applied both in the sender component and/or in the receiver component. Preferably, an orthogonally arranged triplet of magnet coils is used both in the sender as in the receiver component.

In case that such a triplet of orthogonally oriented magnetic coils would be used in the sender component, to generate a magnetic field for transmitting the trigger signal, it can be shown that by means of activating different combinations of said orthogonally oriented magnetic coils, differently oriented magnetic fields will be generated. This implies that for a coil triplet, 7 $(=2^3-1)$ differently orientated magnetic fields can be generated, amongst which one particular combination of activated coils can be chosen to achieve the highest amplitude of measured signal at a magnetic coil of the receiver component.

In case that such a triplet of orthogonally oriented magnetic coils would be used in the receiver component, it can be shown that there will always be a detectable signal in at least one of the orthogonally oriented magnetic coils of the receiver component.

The preferred combination of coils to be activated in the sender component in order to achieve the optimal trigger signal amplitude can be conveniently tested by iterating through the different activated coil combinations. This testing cycle has to be understood as a calibration step to find the optimal activation and read-out configuration of the coil triplets. This preferred coil combination, which can be the activation of a single coil up to all 3 coils at the same time, can then be used as the preferred trigger signal for a particular setup.

For this scenario to work, the receiver component has to be signalled and made aware of an upcoming calibration cycle, during which it can expect to detect different magnetic field strengths depending on the combination of coils being activated. These measurements are then recorded and afterwards compared with each other in order to select the preferred combination for triggering. The data about the configuration of choice has to be transferred back to the sender component for preparing a future trigger action offering the optimal trigger signal amplitude.

Since this technique requires a bidirectional communication for transferring the configuration data between sender component and the receiver component, a communication means [211] and [311] has to be foreseen between both components. In a preferred embodiment, this communication means is a standard communication module capable of supporting Wi-Fi or Bluetooth, or alike.

Said communication means is not restricted by the same latency requirement as for the trigger signal itself, as it only serves to communicate parameter data relating to the initiation of the calibration cycle (or pre-synchronisation mode) and the feedback of the results of said calibration cycle, between the 2 components. This communication may be done in an asynchronous way.

In another embodiment, the communication of above mentioned configuration data may also be contemplated by means of encoding a digital signal into the alternating magnetic field. In this case, a sequence of on-off pulses is used to encode information. The pulse length of a single bit of digital information would in this case be chosen to be at least 10× the period of the alternating field. The information would in this case only flow in one direction only from the sender component to the receiver component (no bi-directional communication is possible).

The different steps of how such a system would work are listed below:

1) The microcontroller of the sender component sends a command (using the wireless communication module [211], or by means of encoding the signal into the alternating magnetic field) to signal the microcontroller of the receiver component that it should be set to a calibration mode; this command may include parameters that define which functions of the digital X-ray sensor should be configured and activated upon triggering (the digital X-ray sensor may support different functions which should be chosen in advance).

2) The microcontroller of the sender component awaits a handshake or confirmation message from the receiver component (which is integrated in or connected to the digital X-ray sensor) signalling its readiness. This handshake or confirmation message is passed on to the generator allowing it to prepare itself for an exposure (this communication is performed using the wireless communication modules).

3) The microcontroller of the receiver component confirms pre-synchronization mode (via Wi-Fi protocol); this step can include communication with the DR sensor to define the function which shall be executed upon a trigger signal. The receiver component is now ready to detect the calibration signals.

4) To find maximum signal: the sender component systematically powers the magnetic coils in the generator triplet, iterating through the different activated coil combinations (e.g.: coil1 on others off; coil2 on others off; coil3 on others off; coil1&2 on other off . . . coil1&3 on others off . . . all coils on). The time between signals must be large enough to allow Wi-Fi communication between the pulses (>100 ms). The microcontroller of the receiver component analyses the induced voltages and gives feedback about the signal strength to the microcontroller of the sender component (via the Wi-Fi communication means).

5) The microcontroller of the sender component selects the strongest signal and sets the microcontroller of the receiver component to synchronization mode (WiFi protocol). The microcontroller of the receiver component confirms the synchronization mode and readiness to accept a trigger signal (via the WiFi protocol). Now the system is ready to synchronize components and Digital X-ray sensor wirelessly.

6) The microcontroller of the sender component receives a trigger signal from the X-ray systems console or X-ray generator and activates the magnetic coil driver to energize the magnetic preferred coil combination. This produces a single magnetic pulse to trigger the pre-set Digital X-ray sensor function (e.g. start read-out).

7) The electrical signal converters [320] of the different magnetic coils in the receiver component detect the trigger signal on the rising edge of the induced signals—which is the sum of all available receiver coils. The trigger signal threshold is determined upfront from the measurement to select the preferred combination of generator coil(s). (see steps 4-5)

8) When the trigger event is detected, the microcontroller of the receiver component commands the digital or analog trigger module [313] to send a trigger signal to the Digital X-ray sensor electronics to which it is electrically connected. This signal starts the pre-defined Digital X-ray sensor function.

9) The previous steps (5 to 8) can be repeated to record an image sequence of a dynamic imaging sequence.

10) In order to terminate the sequence, the microcontroller of the sender component ends the synchronization mode by sending a Wi-Fi command to the receiver component such that both microcontrollers switch to normal mode.

The method above allows to transmit a single trigger signal between the X-ray system and digital X-ray sensor, or may also be used to transmit consecutive individual trigger signals.

In another embodiment of the method, the transmission of the magnetic trigger signal may be used only to synchronize the two clocks of the X-ray system and of the digital X-ray sensor, after which a timed sequence of programmed exposure events may be communicated over the asynchronous digital data communication means. The actual synchronization of the events will rely on the accurately synchronized clocks. The initiation of the sequence may then be communicated as a time point in the near future by means of the less time-accurate wireless data communication means.

The invention claimed is:

1. A system for synchronizing an X-ray generator and a wireless digital X-ray sensor to initiate capturing of a single digital image or a sequence of digital images, the system comprising:
a sender including a sender microcontroller connected to the X-ray generator and configured or programmed to receive a trigger signal from the X-ray generator; and
a receiver including a receiver microcontroller configured or programmed to trigger the wireless digital X-ray sensor when a predetermined condition in a digital signal stream is detected; wherein
the sender further includes:
a sender magnetic coil that generates a magnetic field $\vec{H}$; and
a sender magnetic coil driver for the sender magnetic coil that applies an electric current to the sender magnetic coil upon activation of the sender magnetic coil driver;
the receiver further includes:
a receiver magnetic coil that converts the magnetic field $\vec{H}$ into a measurable electric current; and
an electrical signal converter for the receiver magnetic coil and including an electric current amplifier and an A/D convertor that converts an amplitude of the measurable electric current into the digital signal stream; and
the predetermined condition in the digital signal stream is defined by exceeding a predetermined threshold value.

2. The system according to claim 1, wherein the sender magnetic coil driver generates an alternating electric current, and the magnetic field $\vec{H}$ is an alternating magnetic field.

3. The system according to claim 2, wherein the alternating magnetic field $\vec{H}$ has a frequency between 10 kHz and 30 MHz.

4. The system according to claim 1, wherein the sender magnetic coil and the receiver magnetic coil include a triplet of orthogonally oriented magnetic coils;
the sender magnetic coil driver includes a sender magnetic coil driver for each of the sender magnetic coils in the triplet; and
the electrical signal converter includes an electrical signal converter for each of the receiver magnetic coils in the triplet.

5. The system according to claim 2, wherein the sender magnetic coil and the receiver magnetic coil include a triplet of orthogonally oriented magnetic coils;
the sender magnetic coil driver includes a sender magnetic coil driver for each of the sender magnetic coils in the triplet; and
the electrical signal converter includes an electrical signal converter for each of the receiver magnetic coils in the triplet.

6. The system according to claim 3, wherein the sender magnetic coil and the receiver magnetic coil include a triplet of orthogonally oriented magnetic coils;
the sender magnetic coil driver includes a sender magnetic coil driver for each of the sender magnetic coils in the triplet; and
the electrical signal converter includes an electrical signal converter for each of the receiver magnetic coils in the triplet.

7. The system according to claim 1, wherein the receiver magnetic coil measures a strength of the magnetic field $\vec{H}$.

8. The system according to claim 1, wherein the sender and the receiver further include bi-directional wireless data communicators that:
communicate, from the sender to the receiver, parameter data that determine an activation sequence and timing;
communicate, from the receiver to the sender, the digital signal stream including the electric current measurement data obtained by the receiver magnetic coil.

9. The system according to claim 2, wherein the sender and the receiver further include bi-directional wireless data communicators that:
communicate, from the sender to the receiver, parameter data that determine an activation sequence and timing;
communicate, from the receiver to the sender, the digital signal stream including the electric current measurement data obtained by the receiver magnetic coil.

10. The system according to claim 3, wherein the sender and the receiver further include bi-directional wireless data communicators that:
communicate, from the sender to the receiver, parameter data that determine an activation sequence and timing;
communicate, from the receiver to the sender, the digital signal stream including the electric current measurement data obtained by the receiver magnetic coil.

11. The system according to claim 1, wherein
the wireless digital X-ray sensor includes the receiver magnetic coil;
an X-ray tube includes the sender magnetic coil; and
the wireless digital X-ray sensor and the X-ray tube include respective inoperative or rest positions that provide optimal magnetic coupling of the receiver magnetic coil and the sender magnetic coil.

12. A method of triggering a wireless digital X-ray sensor upon receipt of a trigger signal initiated by an X-ray generator, the method comprising:
receiving the trigger signal from the X-ray generator with a microcontroller in a sender;
activating a magnetic coil driver with the microcontroller;
generating a current that is applied to a sender magnetic coil by the magnetic coil driver;
generating a magnetic field $\vec{H}$ with the sender magnetic coil;
inducing a measurable electric current in a receiver magnetic coil at a receiver with the magnetic field $\vec{H}$;
converting an amplitude of the measurable electric current into a digital signal stream in the receiver with an electrical signal converter including an A/D-converter connected to the receiver magnetic coil;
receiving the digital signal stream from the electrical signal converter with a receiver microcontroller; and
triggering the wireless digital X-ray sensor upon detecting a predetermined condition in the digital signal stream with the receiver microcontroller; wherein
the predetermined condition in the digital signal stream is defined by exceeding a predetermined threshold value.

13. A method for synchronizing a start of an exposure produced by an X-ray generator with a start of an acquisition cycle for the exposure by a wireless digital X-ray sensor, the method comprising:
communicating an anticipated synchronization time point from a sender to a receiver;
activating a magnetic coil driver with a microcontroller of the sender when a clock time of the sender equals the anticipated synchronization time point;
generating a current that is applied to a sender magnetic coil by the magnetic coil driver;
generating a magnetic field $\vec{H}$ with the sender magnetic coil;
inducing a measurable electric current in a receiver magnetic coil at a receiver with the magnetic field $\vec{H}$;
converting an amplitude of the measurable electric current into a synchronization signal;
setting a clock time of the receiver to equal the anticipated synchronization time point upon receiving the synchronization signal;
communicating an anticipated exposure time point to the sender and the receiver; and
triggering both the X-ray generator and the digital X-ray sensor when the anticipated exposure time point equals both the clock time of the sender and the clock time of the receiver.

14. A method for synchronizing a start of an exposure produced by an X-ray generator with a start of an acquisition cycle for the exposure by a wireless digital X-ray sensor, the method comprising:
communicating an anticipated synchronization time point from a sender to a receiver;
activating a magnetic coil driver with a microcontroller of the sender when a clock time of the sender equals the anticipated synchronization time point;
generating a current that is applied to a sender magnetic coil by the magnetic coil driver;
generating a magnetic field $\vec{H}$ with the sender magnetic coil;
inducing a measurable electric current in a receiver magnetic coil at a receiver with the magnetic field $\vec{H}$;
converting an amplitude of the measurable electric current into a digital signal stream in the receiver with an electrical signal converter including an A/D converter connected to the receiver magnetic coil;
receiving the digital signal stream from the electrical signal converter with a receiver microcontroller;
setting a clock time of the receiver to equal the synchronization time point upon detecting a predetermined condition in the digital signal stream by the receiver microcontroller;
communicating an anticipated exposure time point to the sender and the receiver; and
triggering both the X-ray generator and the digital X-ray sensor when the anticipated exposure time point equals both the clock time of the sender and the clock time of the receiver.

\* \* \* \* \*